(12) United States Patent
Krauth

(10) Patent No.: US 7,847,946 B2
(45) Date of Patent: Dec. 7, 2010

(54) VERIFICATION APPARATUS AND METHODS FOR OPTICAL INSPECTION MACHINE

(75) Inventor: Gary H. Krauth, Hopedale, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 301 days.

(21) Appl. No.: 11/913,625

(22) PCT Filed: May 17, 2006

(86) PCT No.: PCT/US2006/018949

§ 371 (c)(1),
(2), (4) Date: Nov. 8, 2007

(87) PCT Pub. No.: WO2006/124917

PCT Pub. Date: Nov. 23, 2006

(65) Prior Publication Data
US 2008/0186499 A1    Aug. 7, 2008

Related U.S. Application Data

(60) Provisional application No. 60/682,283, filed on May 18, 2005.

(51) Int. Cl.
*G01N 21/55* (2006.01)
(52) U.S. Cl. .................................................. 356/445
(58) Field of Classification Search .......... 356/445–448
See application file for complete search history.

(56) References Cited

U.S. PATENT DOCUMENTS

| | | | |
|---|---|---|---|
| 3,907,503 A * | 9/1975 | Betts et al. ............... | 422/67 |
| 5,305,233 A | 4/1994 | Kawagoe et al. | |
| 5,408,535 A * | 4/1995 | Howard et al. ............. | 382/128 |
| 6,239,445 B1 | 5/2001 | Shaeef | |
| 7,141,212 B2 * | 11/2006 | Catt et al. ................. | 422/61 |

(Continued)

FOREIGN PATENT DOCUMENTS

DE    102004047593    4/2006

(Continued)

OTHER PUBLICATIONS

International Search Report for PCT/US2006/018949 filed May 17, 2006.

*Primary Examiner*—Michael P Stafira
(74) *Attorney, Agent, or Firm*—Noam R. Pollack

(57) ABSTRACT

Apparatus and methods are disclosed for verifying one or more operational conditions of an optical inspection machine. A row of grooves (1-5) that simulate a reagent pad containing a specific type of analytes at known concentrations can be used for verification of the operation of the machine. Apparatus can include a row of grooves (1-5), each with different geometry, configured on an insertable device (20). The insertable device (20) can be positioned so that the row of grooves (1-5) can be illuminated by the readhead of the machine. If the optical inspection machine provides results corresponding to the known type(s) and concentrations of analyte(s), proper operation of the optical inspection machine is indicated. If the simulated type and concentration of specified reagen is not indicated, improper operation is indicated. Measurement error due to non-machine error is indicated when the known type and concentration of the analyte simulated by the rows (1-5) is indicated.

23 Claims, 6 Drawing Sheets

| U.S. PATENT DOCUMENTS | | | | EP | 1293926 | 3/2003 |
|---|---|---|---|---|---|---|
| 2004/0005243 A1 | 1/2004 | Mulhern et al. | | WO | WO02/077620 | 10/2002 |
| 2004/0247491 A1 | 12/2004 | Brock et al. | | WO | WO2005/001453 | 1/2005 |
| 2005/0243321 A1* | 11/2005 | Cohen et al. | 356/432 | | | |

FOREIGN PATENT DOCUMENTS

| EP | 0887421 | 3/2003 |
|---|---|---|

* cited by examiner

VERIFICATION APPARATUS AND METHODS FOR OPTICAL INSPECTION MACHINE

FIELD OF THE DISCLOSURE

This application claims the benefit of U.S. Provisional Application No. 60/682,283 filed 18 May 2005, the contents of which are incorporated herein in there entirety by reference.

FIELD OF THE DISCLOSURE

The present disclosure relates to apparatus for and methods of verifying an operational condition of an optical inspection machine. Even more particularly, the present disclosure relates to use of verification apparatus for establishing optical functionality of reflectance spectroscopy-based machines used in medical diagnostics.

BACKGROUND OF THE DISCLOSURE

It can be useful for various medical diagnostic purposes to utilize a reflectance spectroscope to analyze samples of body fluid, for example, to determine the presence of a particular substance in a person's urine. As is known, reflectance spectroscopy uses the linear relationship between absorbance and concentration of an absorbing species (Beer's law), to determine the contents of a sample. An unknown concentration of an analyte can be determined by measuring the amount of light that a sample absorbs and applying Beer's law. If the absorptivity coefficient of the analyte is not known, the unknown concentration can be determined using a working curve of absorbance versus concentration derived from standards.

Reflectance spectroscopy is the study of light as a function of wavelength that has been reflected or scattered from a solid, liquid, or gas. A conventional reflectance spectroscope, often referred to as a "reflectometer," may be used to determine optical characteristics, e.g., the color seen by an observer, of a sample, such as a urine sample disposed on a white non-reactive reagent pad. By illuminating such a sample and detecting/recording the intensity of the reflected light at specific wavelengths, the sample's optical signature can be correlated to known optical signatures, and thus the sample can be identified as containing one or more particular substances.

For example, laboratory-based reflectance instruments are used to measure important properties and relative levels of key analytes in urine by measuring relative reflectance, usually from various specific pads, on a urine dipstick. Examples of important properties include pH, the presence of blood, and specific gravity. Examples of key urine analytes include, but are not limited to, glucose, urobilinogen, nitrite, and protein. Optical instruments with sufficient resolution can be used to read the relatively thin (about 1 mm in width) colored lines that develop on reagent pads or strips from lateral flow (or chromatographic) immunoassays. Such colored lines are usually due to the specific immunochemical binding of colored particles such as colloidal gold or dye-infused polystyrene microparticles. Examples of lateral flow immunoassays that can be read on an instrument include the qualitative assessment of urinary or serum levels of hGC (pregnancy), the presence of Streptococcus A from throat swabs, and the detection of various drugs of abuse (e.g., cocaine, morphine, barbiturates, amphetamines) observed in urine.

Many optical inspection machines are small enough and inexpensive enough to be usable in physician offices and smaller laboratories, for example, and therefore are able to provide individual doctors, nurses and other caregivers with powerful medical diagnostic tools.

For example, U.S. Pat. No. 5,654,803, which is assigned to the assignee of the present disclosure, discloses an optical inspection machine for determining non-hemolyzed levels of occult blood in urine using reflectance spectroscopy. The machine is provided with a light source for successively illuminating a plurality of different portions of a reagent pad on which a urine sample is disposed, and a detector array for detecting light received from the reagent pad and generating a plurality of reflectance signals in response to light received from a corresponding one of the different portions of the reagent pad. The machine is also provided with means for determining whether the magnitude of one of the reflectance signals is substantially different than the magnitude of another of the reflectance signals. Where the body-fluid sample is urine, this capability allows the machine to detect the presence of non-hemolyzed levels of occult blood in the urine sample.

U.S. Pat. No. 5,877,863, which is also assigned to the assignee of the present disclosure, teaches an optical inspection machine for inspecting a liquid sample, such as urine, using reflectance spectroscopy. The machine includes a readhead for illuminating a target area substantially uniformly via only a single light-emitting diode and receiving light from the target area so that reagent tests may be performed. The readhead is provided with a housing, first and second light sources mounted in a fixed position relative to the housing, a light guide mounted to receive light from each of the light sources which conveys, when only one of the light sources is illuminated, substantially all of the light from the light source to illuminate a target area substantially uniformly, and a light detector coupled to receive light from the target area. Each of the first and second light sources is composed of only a single light-emitting diode for emitting substantially monochromatic light of a different wavelength.

The optical inspection machines can provide individual doctors, nurses and other caregivers with powerful medical diagnostic tools. These optical inspection machines, however, are not small enough to make shipping the machines (e.g., via the U.S. postal service, or express mail services) between a physician's office or laboratory and the manufacturer convenient and inexpensive. Having a tool and method for verifying the performance of, or troubleshooting, an optical inspection machine in-situ, e.g., at a physician's office or laboratory, could prevent unnecessary shipment of machines for repair when incorrect readings are produced not by a malfunctioning or defective machine but by non-machine problems such as operator error or damaged or defective reagent strips.

Co-pending International Patent Application Serial No. PCT/US2004/017344 (Publication No. WO 2005/001444), which is assigned to the assignee of the present disclosure and which is incorporated herein by reference, discloses an apparatus for verifying proper operation of an optical inspection machine. The apparatus includes a row of colored segments that simulate reagent pads containing known types of analytes at known concentrations positioned so that the row of colored segments can be illuminated by the readhead of the optical inspection machine. If the optical inspection machine provides results that correspond to the known types and concentrations of analytes, then the machine is operating properly. According to one embodiment, the rows of colored segments are colored ink provided on a paper insert.

What is still desired are new and improved apparatus and methods for verifying proper operation of an optical inspection machine, such as those used in medical diagnostics. Preferably, the new and improved apparatus and methods will provide the ability to verify the operation of optical inspection machines using a compact, portable, easy-to-use and inexpensive device. The new and improved apparatus will also be thermally and optically stable and relatively easy to re-produce on a consistent basis.

SUMMARY OF THE DISCLOSURE

Embodiments of the subject disclosure are directed to apparatus and methods for verifying one or more operational conditions, such as a condition of proper operation, of optical inspection machines, such as those used in medical diagnostics.

An exemplary embodiment of the apparatus includes an insertable device with a row of grooves that simulate one or more reagent pads containing one or specific analytes at known concentrations. The grooves can each have a different geometry, e.g., depth, relative to other grooves in the row. In operation, the grooves are positioned within the optical inspection machines so that they can be illuminated by the readhead of the optical inspection machine. The optical inspection machine is operated to illuminate the row of grooves and detect the reflected optical signals. One or more operational conditions of the optical inspection machine can consequently be determined. For example, if the optical inspection machine provides results corresponding to the known type(s) and concentrations of analyte(s) simulated by the row of grooves, proper operation of the optical inspection machine is indicated. If the simulated type and concentration of specified reagent is not indicated, improper operation, e.g., misaligned optical train, is indicated. Measurement error due to other than machine error may be indicated when the known type and concentration of the simulated analyte simulated by the rows is indicated by the inspection machine. The insertable device can be a cassette.

Embodiments of methods according to the present disclosure generally include inserting the apparatus into the optical inspection machine so that the grooves can be illuminated by the readhead of the optical inspection machine. The optical inspection machine is then operated, and the results provided by the optical inspection machine are compared to the known types and concentrations of analytes simulated by the grooves.

If the optical inspection machine produces readings that match the known types and concentrations of analytes replicated by the grooves, then the machine is operating properly and unexpected readings provided by the machine during normal use are produced not by a malfunction or defect of the machine, but by non-machine problems such as operator error or damaged or defective reagent strips. However, if the machine produces readings that do not match the known types and range of concentrations of analytes replicated by the grooves, then the machine itself is malfunctioning, damaged or defective, and needs to be repaired.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference character designations represent like elements throughout, and wherein.

DETAILED DESCRIPTION OF EXEMPLARY EMBODIMENTS

The present disclosure is directed to apparatus for and methods of verifying an operational condition of optical inspection machines that inspect samples of body fluid for medical diagnostic purposes. Such apparatus can be compact, portable, easy-to-use and inexpensive. Apparatus according to the present disclosure can further be used to establish the optical functionality of an optical inspection machine in situ, without the need to move the machine. In addition, verification apparatus and methods according to the present disclosure can provide thermal and optical stability and reproducibility of results on a consistent basis.

FIGS. 6-9 depict aspects of exemplary embodiments of the present disclosure configured and arranged as inserts for use with optical inspection machines.

Figure 1:
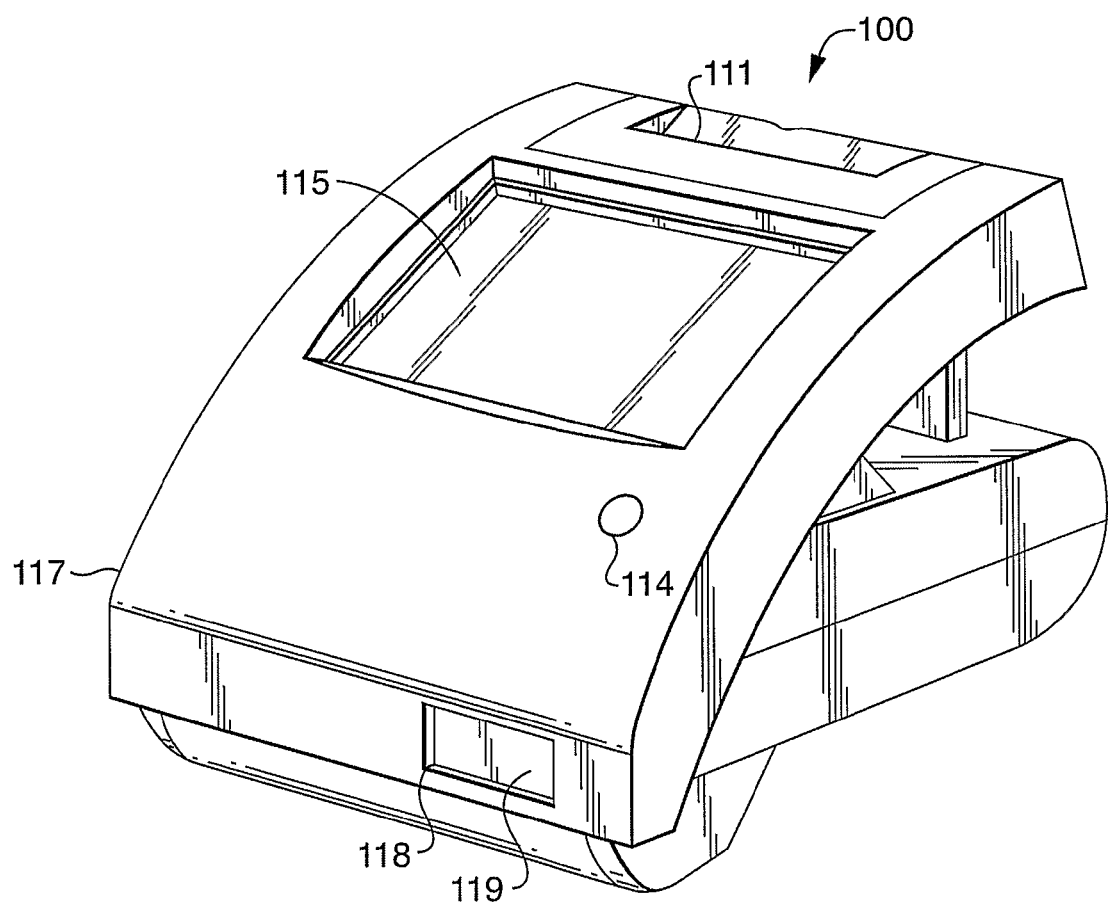
FIG. 1 is a perspective view of an optical inspection machine of the prior art used to perform various tests of a body fluid sample, which may be used with apparatus and methods according to the present disclosure.
Figure 2:
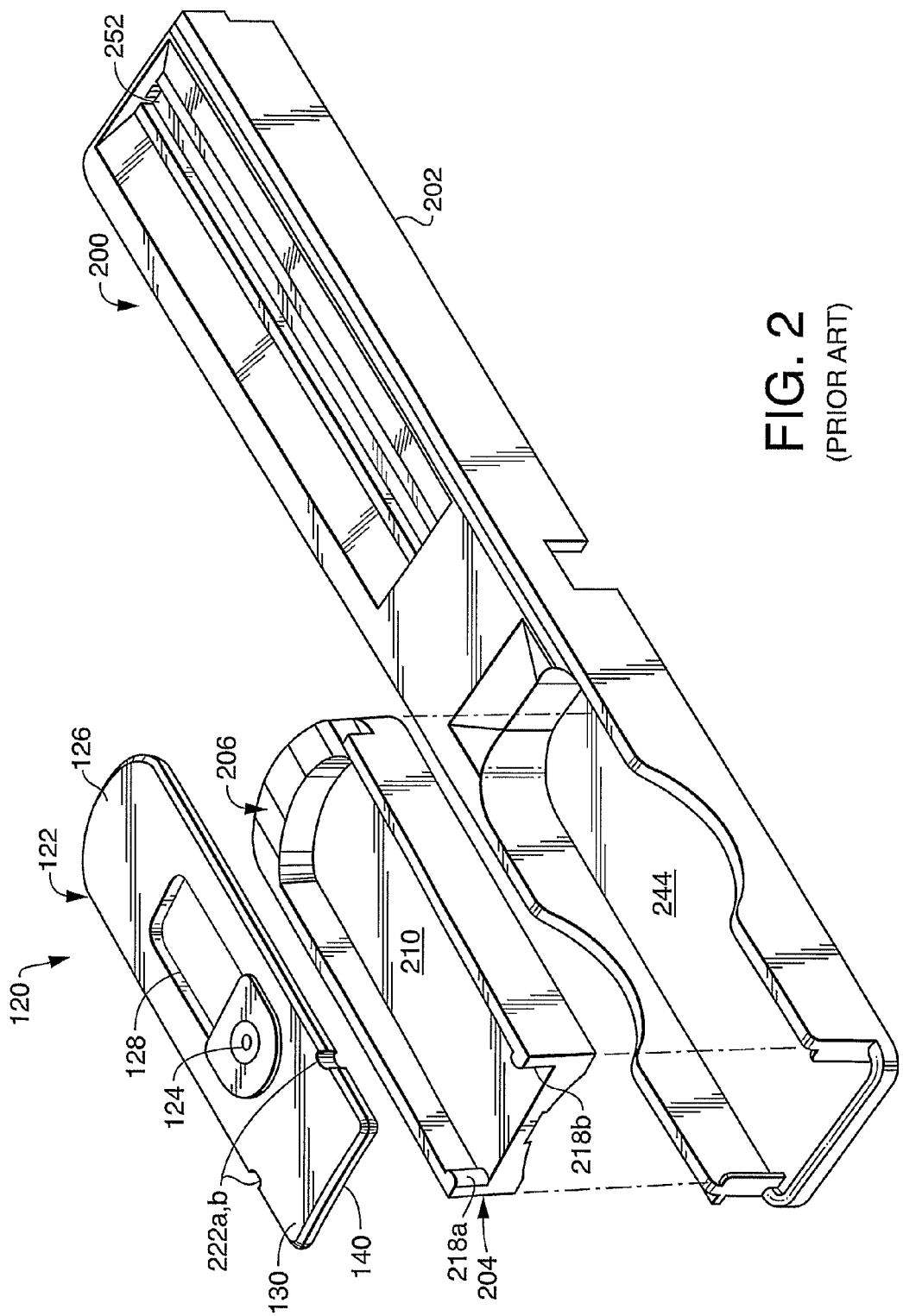
FIG. 2 is an end perspective, exploded view of a tray assembly for use with the machine of FIG. 1, wherein the assembly includes a support tray and an insert, and wherein the insert is shown being positioned in the support tray with a first surface facing upwardly so that a reagent cassette may be held by the insert in the support tray, as shown.
Figure 3:
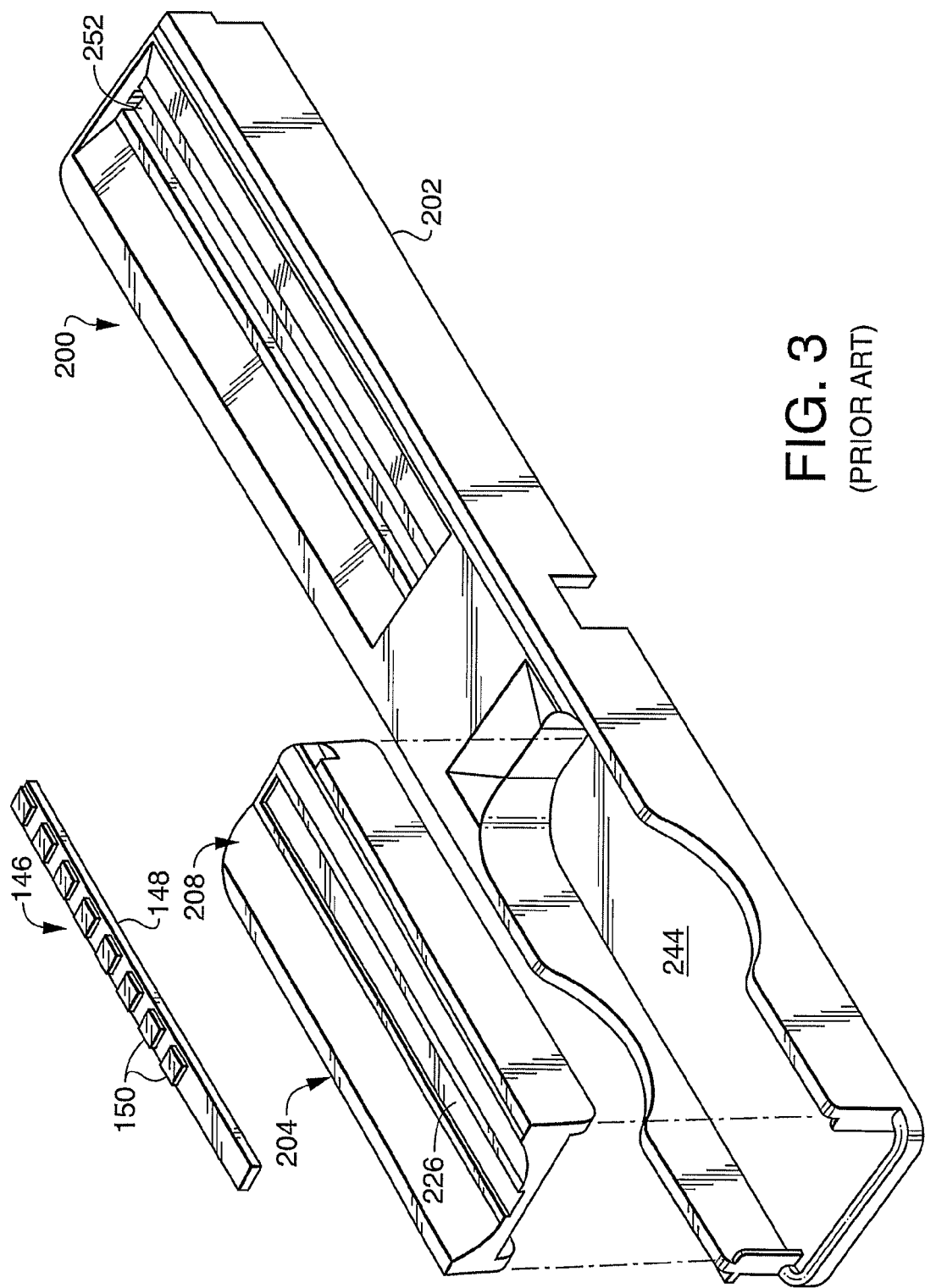
FIG. 3 is an end perspective, exploded view of the assembly of FIG. 2, wherein the insert is shown being positioned in the support tray with a second surface facing upwardly so that a reagent strip may be held by the insert in the support tray, as shown.
Figure 4:
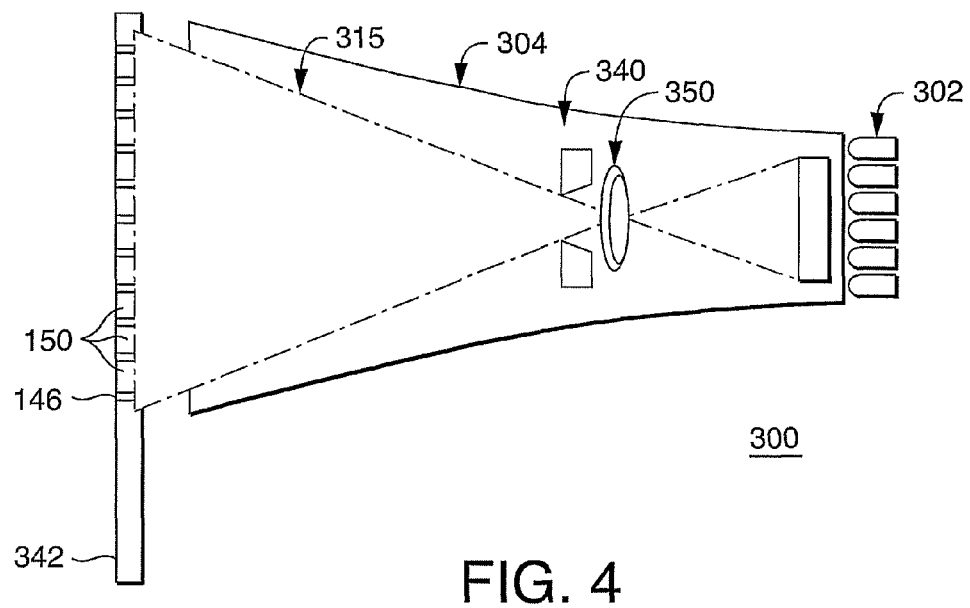
FIG. 4 is a top plan view of a diagram illustrating a readhead of the optical inspection machine of FIG. 1.
Figure 5:
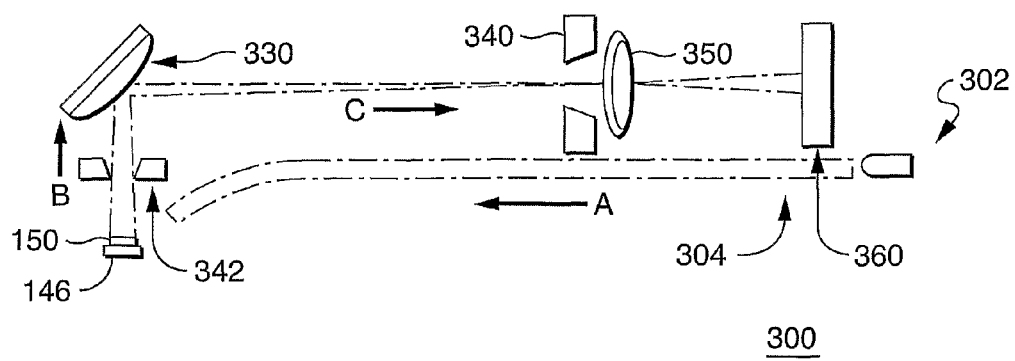
FIG. 5 is a side elevation view of a diagram illustrating the readhead of FIG. 4.

Embodiments of the present disclosure, including those shown in FIGS. 6-9, may be used to verify operational conditions of optical inspection machines and components, such as shown in FIGS. 1-5. The machine 100 of FIG. 1 is a reflectance spectroscope, or "reflectometer," for optically inspecting liquid samples such as body fluid samples, placed on a liquid carrier, such as a reagent cassette 120 or a reagent strip 146, examples of which are shown in FIGS. 2 and 3, respectively. FIGS. 4 and 5 show an exemplary embodiment of a readhead 300 of the inspection machine 100.

Optical Inspection Machine

The particular optical inspection machine 100 shown in FIG. 1 represents a CLINITEK STATUS® Urine Chemistry Analyzer available from Bayer Corporation, Diagnostics Division, of Tarrytown, N.Y. Embodiments of the present disclosure, however, can also be used with other optical inspection machines, including, but not limited to, a CLINITEK® 50 Urine Chemistry Analyzer, which is also available from Bayer Corporation, Diagnostics Division, of Tarrytown, N.Y., and which is described in U.S. Pat. Nos. 5,654,803; 5,945,341; and 6,239,445, which are assigned to the assignee of the present disclosure and incorporated herein by reference.

The inspection machine 100 of FIG. 1 generally includes a printer 111, an on/off switch 114, and a touch-screen display 115 for user input and for displaying various messages to a user relating to the operation of the inspection machine 100. The inspection machine 100 also has a housing 117 with an opening 118 formed therein into which a tray assembly 200 shown in FIGS. 2 and 3 may be retracted. The opening 118 includes a door 119 that opens upon the tray assembly 200 being extended out of the opening 118.

Reagent Cassette and Reagent Strip

The tray assembly 200 is for supporting the reagent cassette 120 or the reagent strip 146 as shown in FIGS. 2 and 3, and includes a support tray 202 and an insert 204 that fits into the support tray with one of a first surface 206, adapted to hold the reagent cassette 120, and a second surface 208, adapted to hold the reagent strip 146, facing upwardly so that one of the reagent cassette 120 and the reagent strip 146 can be held by the insert 204 in the support tray 202. The tray assembly 200 is described in greater detail in co-owned and co-pending U.S. patent application Ser. No. 10/821,441, filed on Apr. 9, 2004, which is incorporated herein by reference in its entirety.

Referring to FIG. 2, the reagent cassette 120 may be a disposable, single-use cassette for doing a lateral flow pregnancy immunoassay test, for example, in the conventional manner. In the exemplary embodiment shown, the reagent cassette 120 has a housing including a top piece 130, which defines a window 128, and a bottom piece 140. During assembly of the housing 122, the bottom piece 140 is secured to the top piece 130. The reagent cassette 120 has an opening or well 124 in the top piece 140 into which a body fluid sample, such as urine, is placed. The housing 122 of the reagent cassette 120 contains a reagent strip (not shown) which may react with the body fluid sample placed in the well 124. Depending on the results of the test, the reagent strip may change color (e.g., a colored stripe may appear), which is determinable from viewing the reagent strip through a window 128 of the reagent cassette 120.

Referring to FIG. 3, the reagent strip 146 may have a thin, non-reactive substrate 148 on which a number of reagent pads 150 are fixed. Each reagent pad 150 may be composed of a relatively absorbent material impregnated with a respective reagent, each reagent and reagent pad 150 being associated with a particular test to be performed. When urinalysis tests are performed, they may include, for example, a test for leukocytes in the urine, a test of the pH of the urine, a test for blood in the urine, etc. When each reagent pad 150 comes into contact with a urine sample, the pad changes color over a time period, depending on the reagent used and the characteristics of the urine sample. The reagent strip 146 may be, for example, a MULTISTIX® reagent strip commercially available from Bayer Corporation, Diagnostics Division, of Tarrytown, N.Y., and the reagent strip 146 may include, but is not limited to, reagent pads 150 for: leukocytes, glucose, bilirubin, ketone, specific gravity, nitrite, pH, protein, urobilinogen, blood, albumin, and creatinine.

During use, the insert 204 of the tray assembly 200 is removable from the support tray 202 and can be turned over and re-inserted into the support tray 202 depending upon which of the reagent cassette 120 and the reagent strip 146 is to be used with the tray assembly 200. Referring to FIG. 2, the surface 206 of the insert 204 has a recess 210 shaped to receive the reagent cassette 120. An end wall of the recess 210 is curved to match a curved end wall of the reagent cassette 120, to ensure that a user correctly orients the reagent cassette 120 within the insert 204. The insert 204 also includes orientation features such as bosses 218a, 218b that are received in, respectively, indents 222a, 222b in the reagent cassette 120 to prevent the reagent cassette 120 from sliding out of the insert 204. Alternatively, the bosses can be provided on the reagent cassette 120 and the indents in the insert 204. The bosses 218a, 218b of the recess 210 are provided in slightly different sizes or shapes, and the indents 222a, 222b of the reagent cassette 120 are also provided in slightly different sizes or shapes, which match the bosses 218a, 218b, to prevent the reagent cassette 120 from being inserted into the insert 204 upside down.

Referring to FIG. 3, a second surface 208 of the insert 204 has an elongated channel 226 sized to accommodate the reagent strip 146. As shown in FIGS. 2 and 3, the support tray 202 includes a compartment 244 for receiving the insert 204, and an elongated channel 252 for receiving a white calibration strip (not shown).

During an inspection procedure the tray assembly 200 and one of a reagent cassette 120 and a reagent strip 146 is moved between an outwardly extended position and an optical inspection position in which the tray assembly 200 is retracted inwardly into the housing 117 of the inspection machine 100 and into the readhead 300 of the machine.

Readhead

Referring to FIGS. 4 and 5, the readhead 300 can include a number of light-emitting diodes (LEDs) 302 for irradiating a sample with light at a number of different wavelengths. For example, the signals transmitted by the LEDs can be blue light at a wavelength of about 470 nanometers (nm), green light at a wavelength of about 525 nm, green light at a wavelength of about 565 nm, red light at a wavelength of about 625 nm, red light at a wavelength of about 660 nm, and an infrared (IR) signal at a wavelength of about 845 nm. It should be understood that these wavelengths are approximate, and that the LED manufacturers typically provide LEDs that operate within a specified range of light output. In operation, only one of the LEDs 302 functions at a time, and the illumination provided by that single LED 302 is sufficient to uniformly illuminate the reagent strip 146 to an extent that allows a detector array 360 to detect enough light from the reagent strip 146 to have the reagent tests described above satisfactorily performed. The detector array 360 may include any number of suitable photodetectors, e.g., photodiodes operative at one or more wavelengths of the source LEDs.

Test signals from the LEDs 302 are transmitted through a guide 304 in the direction of arrow A, as shown in FIG. 5. The test signals from the guide 304 impinge on one of a reagent cassette or a reagent strip positioned in the readhead 300 on the tray assembly (not shown in FIGS. 4 and 5). In FIGS. 4 and 5, a reagent strip 146 is shown positioned in the readhead 300. Light reflected from the test strip in the direction of arrow B, as shown in FIG. 5, passes through an aperture 342, after which it impinges on convex mirror 330, which redirects and focuses the reflected signals in the direction of arrow C, as shown in FIG. 5. In this arrangement, due to the orientation of the mirror 330, the optical path of the reflected signals takes an approximate 90° turn after leaving the test strip 146. The reflected signals propagating in the direction of arrow C pass through aperture 340 and converge at an aspheric diverging lens 350. The aspheric lens 350 spreads the reflected signals, which then impinge on the detector array 360. As will be appreciated by those skilled in the art, the shapes and arrangement of mirrors and lenses need not specifically conform to or be limited to those shown in the illustrative embodiment of FIGS. 4 and 5.

The detector array 360 receives the optical signals reflected from the reagent cassette or strip of the test pads 150. The reflected image of the reagent cassette or strip of the test pads 150 as detected at the detector array 360 represents the reflectance values of the reagent cassette or strip. The individual detectors of the detector array 360 can convert the received optical signals into electrical signals for image processing. According to one exemplary embodiment, the detector 360 is a charge coupled device (CCD) including a linear arrangement of 2048 detectors configured to receive the reflected signals. Signals produced by the detector array may be used on a detector-by-detector basis to form a usable representation (e.g., an array of discrete, digitized values) of the test pads 150. Picture element (pixel) data can be grouped and associated with individual pads 150 on the test strip 146. As a result, the test strip is imaged and wavelength-specific reflectance values for each pad are determined, for example, according to the following description.

The received reflected signals, as an image of the test strip at various wavelengths, represent an optical spectral signature of the test pad. A spectral signature is a plot of reflectance (e.g., as a percentage of the incident light) versus wavelength for a given material. The reflected signals received by the detectors can be translated into data, e.g., in digital form, representing the reflectance values and optical signature. Each reflectance value is a function of the wavelength of the light transmitted from the source and the make-up of the test pad from which the signal was reflected. Accordingly, different samples and test pads can have different spectral signatures. For reflected signals received at the detector, the presence of a material associated with a particular spectral signature can be determined by comparing the reflected signals with a set of know spectral optical signatures. The verification apparatus 20 shown in FIG. 6 and method for verifying provided by the present disclosure can accordingly be used to ensure that the readhead 300 is functioning properly, as described in further detail below.

Verification Apparatus and Methods

Figure 6:
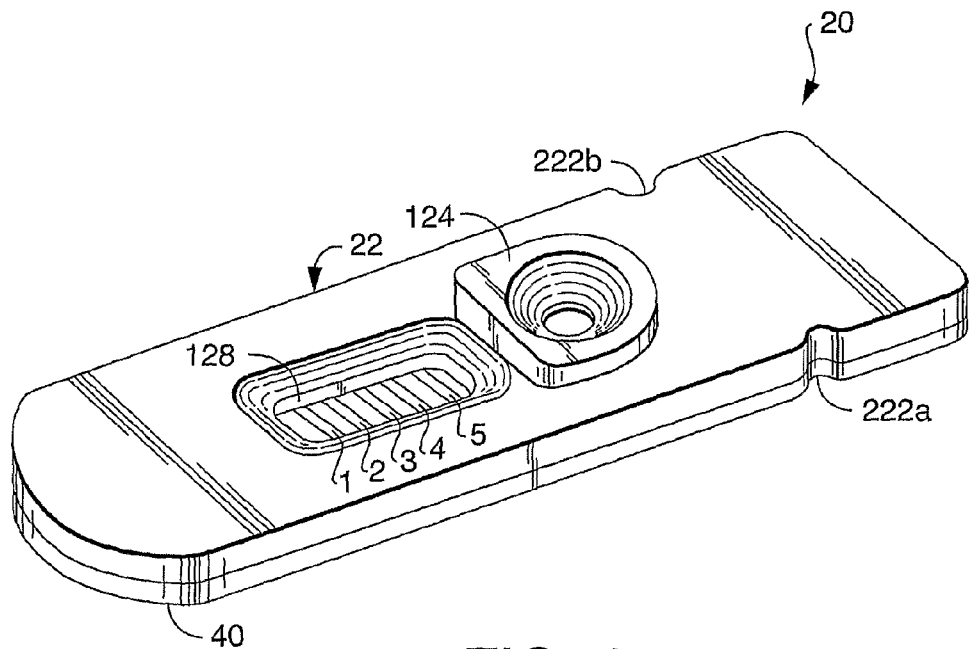
FIG. 6 is a top perspective view of an exemplary embodiment of a verification apparatus constructed in accordance with the present disclosure, which can be used, for example, to verify proper operation of the optical inspection machine of or similar to FIG. 1.
Figure 7:
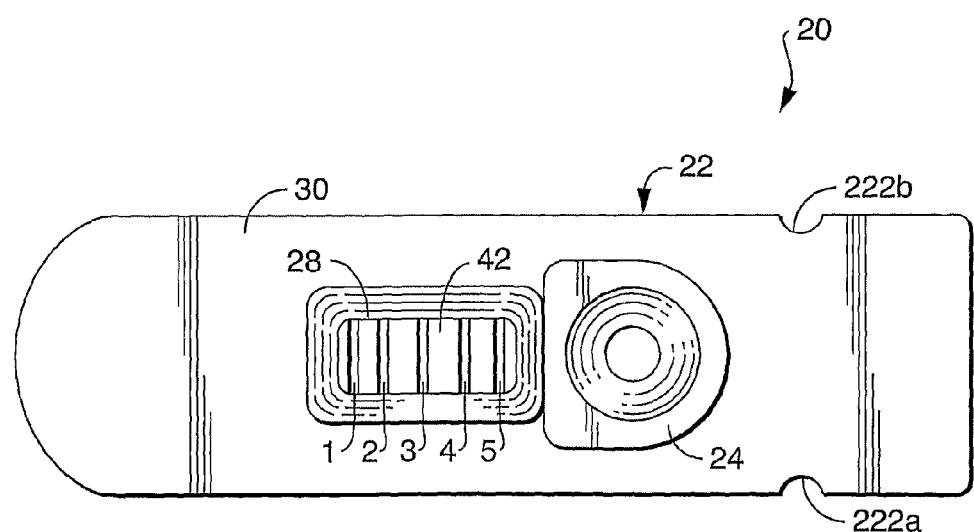
FIG. 7 is a top plan view of the verification apparatus of FIG. 6.
Figure 8:
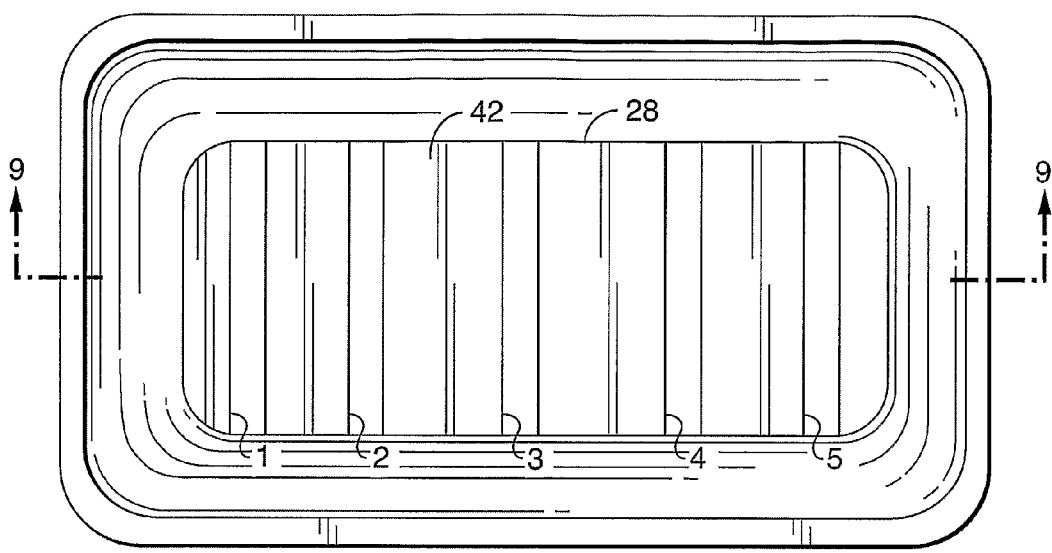
FIG. 8 is an enlarged top plan view of a portion of the verification apparatus of FIG. 6.
Figure 9:
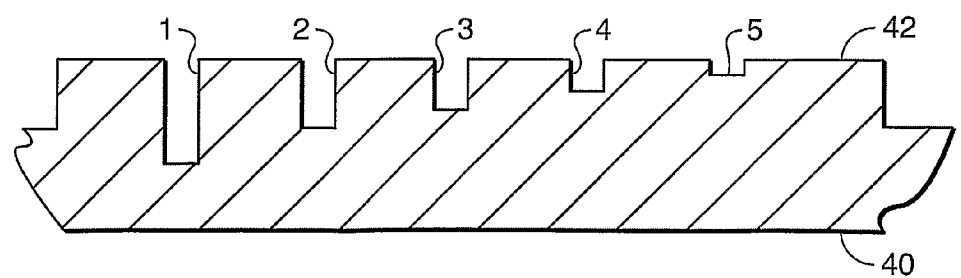
FIG. 9 is a sectional view of a portion of a bottom piece of the verification apparatus of FIG. 8 as taken along line 9-9.

Embodiments of the present disclosure are directed to verification apparatus and methods that can be used to determine or adjust an operational condition of an optical inspection machine. FIGS. 6-7 depict an exemplary embodiment of verification apparatus in accordance with the present disclosure including an insertable device configured as an insert or cassette 20. Referring o FIG. 6, the verification apparatus, or cassette, 20 can include a housing 22 adapted to be received within a readhead of an optical inspection machine, e.g., 300 of the optical inspection machine 100. The verification apparatus 20 also includes a row of grooves 1-5, also shown in FIGS. 8 and 9, that, when illuminated by the readhead 300 or other suitable optical source, simulate reflectance signatures of reagent pads containing known concentrations of specific analytes. The row of grooves 1-5 is positioned on the apparatus 20 so that the grooves 1-5 can be illuminated by the LEDs of the readhead 300 of the optical inspection machine 100 when the cassette 20 is placed in the machine. Verifying proper operation and calibration of the optical inspection machine In exemplary embodiments, as shown in FIGS. 8-9, the grooves 1-5 can vary in depth by successively increasing along a dimension of the cassette. In addition, the grooves 1-5 can have equal widths and may have the same center-to-center spacing between adjacent grooves. Alternatively, the grooves 1-5 can be provided with unequal widths and be unequally spaced apart if desired, and the depths of the grooves 1-5 can be varied as desired. The grooves 1-5 may be formed by any suitable techniques, e.g., cut using standard machine shop equipment, such as a Hurco CNC milling machine.

In the optical inspection machine 100 reflectance across a surface of the verification cassette 20 where the grooves 1-5 are formed can be measured, and the reflectance amplitudes of the grooves may be calculated. For example, the reflectance amplitudes may be calculated from the difference between the groove minimum and a baseline using parameters typical for measuring colored particle (e.g., gold sol) lines in lateral flow immunoassays.

The grooves 1-5 can serve as a reference and may be used to verify proper operation of the following functions of the machine: the machine's optical train alignment, the machine's optical linearity, and the machine's calibration strip precision.

A method for verifying proper operation of the optical inspection machine 100 according to the present disclosure generally includes inserting the cassette 20 into the optical inspection machine 100 so that the row of grooves 1-5 can be illuminated by the readhead 300 of the optical inspection machine. The tray assembly 200 may be used for insertion of the cassette 20. The optical inspection machine 100 is then operated, and the results provided by the optical inspection machine 100 are compared to the known types and concentrations of analytes simulated by the row of grooves 1-5. If the machine 100 produces readings that match the known types and concentrations of analytes replicated by the row of grooves 1-5, then it will be known that the machine is operating properly and incorrect readings provided by the machine during normal use are produced not by a malfunction or defect of the machine, but by non-machine problems such as operator error or damaged or defective reagent strips. If, however, the machine 100 produces readings that do not match the known types and concentrations of analytes replicated by the row of grooves 1-5, then it will be known that the machine itself is malfunctioning, damaged or defective, and needs to be repaired.

Verification apparatus and methods of the present disclosure can be used to verify the performance of, or troubleshoot, an optical inspection machine at a physician's office or laboratory. Such verification apparatus and methods can be used to prevent the unnecessary shipment of machines back to the manufacturer when incorrect readings are produced not by a malfunctioning or defective machine but by non-machine problems such as operator error or damaged or defective reagent strips.

Embodiments of verification apparatus and methods according to the present disclosure can also be used by physician office or laboratory personnel as part of a quality control program to confirm proper operation of an optical inspection machine, for example, by conducting verification tests using the verification apparatus and method on a scheduled basis and recording the results of each test. In addition, the results can be used to correct for normal machine to machine variation to thereby increase the precision of results provided by each machine.

In the exemplary embodiment shown in FIGS. 6 and 7, the verification apparatus is configured as a cassette 20 that is similar in shape and size to the insert or reagent cassette 120 of FIG. 2, such that the cassette 20 can be used with the tray assembly 200 of FIG. 2. In particular, the housing 22 of the cassette 20 includes orientation features such as indents 222a, 222b that receive the bosses 218a, 218b of the insert 204 of the tray assembly 200 (shown in FIG. 2) to prevent the cassette 20 from sliding out of the insert 204 and to ensure that the cassette 20 is correctly oriented in the insert 204. Alternatively, the bosses can be provided on the cassette 20 and the indents in the insert 204. The bosses 218a, 218b and the indents 222a, 222b are provided in slightly different sizes or shapes to prevent the cassette 20 from being inserted into the tray assembly 200 upside down.

In the exemplary embodiment shown, the housing 22 of the cassette 20 includes a top piece 130, which can be the same top piece 130 used in the reagent cassette 120 of FIG. 2. The top piece 130 includes the window 128. The housing 22 of the cassette 20 also includes a bottom piece 40 that is similar, but not identical to, the bottom piece 140 of the reagent cassette 120 of FIG. 2. During assembly of the housing 22, the bottom piece 40 is secured to the top piece 130, for example, in a snap-fit manner using prongs of the top piece 130, which are received in corresponding bores of the bottom piece 40. As shown in FIGS. 6-9, the bottom piece 40 includes a unitarily formed insert 42 and the grooves 1-5 are etched in the insert 42.

In an alternative embodiment, the housing 22 of the cassette 20 can be provided with a bottom piece that is identical to the bottom piece 140 of the reagent cassette 120 of FIG. 2, and the cassette 20 can further include an insert comprising an elongated strip of paper, plastic, or metal (or other suitable material) having the grooves 1-5 etched thereon. In such an embodiment, the bottom piece 140 would include features that act to correctly position the insert with respect to the window 128 of the top piece 130 upon assembly of the housing 122.

Experimental measurement of reflectance amplitudes were calculated for an exemplary embodiment, as indicated in the following Table 1.

TABLE 1

| Depth (inches) | Count | Average Amplitude | Standard Deviation |
| --- | --- | --- | --- |
| 0.000 | 50 | 0.180 | 0.119 |
| 0.002 | 50 | 1.58 | 0.321 |
| 0.003 | 50 | 1.75 | 0.294 |
| 0.005 | 50 | 2.61 | 0.464 |
| 0.010 | 50 | 4.58 | 0.527 |
| 0.020 | 50 | 9.27 | 0.637 |

Table 1 shows a summary of results measured for an exemplary embodiment, in which multiple cassettes 20 were fabricated from the bottom portions of ten CLINITEST® cassettes, commercially available from Bayer Corporation, Diagnostics Division, of Tarrytown, N.Y. Each cassette included a row of five grooves 1-5 made with a bit having a width of 0.015 inches (15 mils) and a flat space, corresponding to a groove of zero depth. As indicated in Table 1, the grooves of the exemplary embodiment had respective depths of 0.002 inches, 0.003 inches, 0.005 inches, 0.010 inches, and 0.020 inches.

Reflectance across the surface of the raised platform of each cassette was measured using five separate CLINITEK STATUS® instruments. Fifty measurements were taken for each groove depth, with five measurements from each instrument being recorded from each of the ten cassettes. The calculated average reflectance amplitudes for each groove (or line) and corresponding standard deviation of the measurements are indicated in Table 1 for each groove. The groove (or line) reflectance amplitude was shown to be a linear function of etched depth, with a high correlation coefficient ($r=0.988$).

With continued reference to Table 1, grooves having a depth of 0.003 may produce reflectance amplitudes that represent the approximate minimum intensity that the majority of visual readers would report seeing in a lateral flow assay using colored gold sol particles. Thus, a groove having a depth of 0.003 inches may represent a minimum observable weak line of colored particles, as amplitudes near of less than 1 are typically not visually observable by the majority of the population. As described previously, the etched lines or grooves could serve as a reference for assessing optical performance and/or track performance as part of a clinical laboratory's quality control procedures.

Accordingly, embodiments of the present disclosure can provide a determination of one or more operational conditions of an optical inspection machine. Embodiments may function as verification tools that indicate whether an optical inspection machine is functioning correctly. Such verification tools and methods may be used to verify proper operation of functions of the optical inspection machine, including optical train alignment, light emitting diode color accuracy, optical linearity, colored line detection and accuracy, and calibration strip precision. Such verification tools and methods can also be used by a physician's office or laboratory as part of a quality control program to confirm proper operation of the optical inspection machine by conducting verification tests using the verification tool and method on a scheduled basis and recording the results of each test. Results from such apparatus and methods can be re-produced on a consistent basis, and can also be used to correct for normal machine to machine variation and thereby to increase the precision of results provided by each machine. Embodiments are thermally and optically stable.

Numerous further modifications and alternative embodiments of the present disclosure will be apparent to those skilled in the art in view of the foregoing description. For example, although the exemplary embodiment of the cassette 20 shown in FIG. 6 includes a housing 22, it should be understood that verification apparatus constructed in accordance with the present disclosure do not have to comprise a cassette including a housing, but can simply comprise an insertable device/structure such as a strip similar to the test strip 146 shown in FIG. 3. In such embodiments, for example, the insertable device/structure could comprise an elongated strip of paper, plastic, or metal (or other suitable material) with the grooves 1-5 etched thereon.

The exemplary embodiments shown and discussed in this specification are therefore to be construed as illustrative only, and are for the purpose of teaching those skilled in the art the best modes of carrying out the disclosure. The details of the apparatus and method may be varied substantially without departing from the spirit of this disclosure, and the exclusive use of all modifications which come within the scope of the appended claims is reserved.

What is claimed is:

1. An apparatus for verifying proper operation of an optical inspection machine having a readhead, the apparatus comprising: an insertable device configured and arranged for insertion into an optical inspection machine; and a row of spaced-apart grooves disposed in a surface of the insertable device, wherein the row of grooves is configured and arranged to simulate a reflection at the readhead of the optical inspection machine of a reagent pad having a known concentration of a specific analyte.

2. An apparatus as defined in claim 1, wherein the grooves are etched.

3. An apparatus as defined in claim 1, wherein the grooves vary in depth.

4. An apparatus as defined in claim 3, wherein the depth of each of the grooves successively increases along one dimension of the insertable device.

5. An apparatus as defined in claim 1, wherein the grooves have equal widths.

6. An apparatus as defined in claim 1, wherein the grooves are equally spaced apart.

7. An apparatus as defined in claim 1, further comprising a top piece defining a window, and a bottom piece secured to the top piece and including a raised insert positioned below the window of the top piece, wherein the row of grooves are formed in the raised insert.

8. An apparatus as defined in claim 1, wherein the insertable device is a cassette, and the cassette includes a housing with orientation features that mate with orientation features of a tray assembly for guiding the cassette into the optical inspection machine, so that the cassette can be correctly oriented in the tray assembly.

9. An apparatus as defined in claim 1, wherein the insertable device is a cassette, and further comprising a tray assembly including a support tray for insertion into the optical inspection machine and an insert that fits into the support tray, and wherein the insert has a surface contoured to receive the cassette.

10. An apparatus as defined in claim 1, wherein the row of grooves is configured and arranged to simulate a reflection at the readhead of the optical inspection machine of a reagent pad having a known concentration of a specific analyte.

11. A system for verifying an operational condition of an optical inspection machine, the system comprising: an insertable device; a row of spaced-apart grooves disposed in a surface of the insertable device, wherein the row of grooves is configured and arranged to simulate a reflection at the readhead of the optical inspection machine of a reagent pad having a known concentration of a specific analyte; and a read head including a light source configured and arranged to illuminate the insertable device and a detector for receiving light reflected from the row of grooves.

12. A system as defined in claim 11, wherein the light source comprises a plurality of light emitting diodes providing light at different wavelengths.

13. A system as defined in claim 11, wherein the detector includes a detector array.

14. A system as defined in claim 11, further comprising a housing adapted to receive the insertable device at an inspection location, wherein the readhead is disposed within the housing.

15. A system as defined in claim 11, further comprising a processor operatively connected to the detector for processing signals received from the detector, wherein the processor is configured and arranged to compare signals from the detector with one or more known optical signatures.

16. A method for verifying proper operation of an optical inspection machine, the method comprising: inserting an insertable device having a row of grooves into an optical inspection machine so that the row of grooves can be illuminated by a readhead of the optical inspection machine, wherein the row of grooves are configured and arranged to simulate a reflection at the readhead of the optical inspection machine of a reagent pad; operating the optical inspection machine; and comparing the results provided by the optical inspection machine to a known concentration of one or more specific analytes simulated by the row of grooves.

17. A method as defined in claim 16, wherein the grooves are etched in a housing of the insertable device.

18. A method as defined in claim 16, further comprising using the row of grooves to confirm that an optical train alignment of the optical inspection machine is correct.

19. A method as defined in claim 16, further comprising using the row of grooves to confirm a calibration strip precision of the optical inspection machine.

20. A method as defined in claim 16, further comprising using the row of grooves to confirm that an optical linearity of the optical inspection machine is correct.

21. A method as defined in claim 16, wherein operating the optical inspection includes detecting a reflected image of the row of grooves.

22. A method as defined in claim 16, further comprising simulating the optical signature of a known concentration of one or more specific analaytes with the row of grooves.

23. A method as defined in claim 16, wherein the insertable device is a cassette.

* * * * *